(12) United States Patent
McAuley et al.

(10) Patent No.: US 11,980,719 B2
(45) Date of Patent: May 14, 2024

(54) HUMIDIFIED GASES DELIVERY APPARATUS AND METHODS FOR CONTROLLING SAME

(71) Applicant: Fisher & Paykel Healthcare Limited, Auckland (NZ)

(72) Inventors: Alastair Edwin McAuley, Auckland (NZ); Yi-Cheng Sun, Auckland (NZ); Jonathan David Harwood, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 353 days.

(21) Appl. No.: 17/445,808

(22) Filed: Aug. 24, 2021

(65) Prior Publication Data

US 2022/0040439 A1     Feb. 10, 2022

Related U.S. Application Data

(60) Continuation of application No. 16/252,339, filed on Jan. 18, 2019, now Pat. No. 11,129,957, which is a
(Continued)

(51) Int. Cl.
*A61M 16/16*     (2006.01)
*A61M 16/00*     (2006.01)
(Continued)

(52) U.S. Cl.
CPC ........ *A61M 16/16* (2013.01); *A61M 16/0051* (2013.01); *A61M 16/0066* (2013.01);
(Continued)

(58) Field of Classification Search
CPC .............. A61M 16/00; A61M 16/0003; A61M 16/0051; A61M 16/0057; A61M 16/0066;
(Continued)

(56) References Cited

U.S. PATENT DOCUMENTS 1,156,145 A    10/1915   Jenkins
3,783,262 A     1/1974   Pile
(Continued)

FOREIGN PATENT DOCUMENTS

DE     102006018423     10/2007
ES       2208807       6/2004
(Continued)

OTHER PUBLICATIONS

International Search Report and Written Opinion; PCT/NZ2010/000263; dated Jun. 14, 2011; 15 pages.

*Primary Examiner* — Joseph D. Boecker
(74) *Attorney, Agent, or Firm* — Knobbe, Martens, Olson & Bear, LLP

(57) ABSTRACT

The invention relates to a method of determining water level in a humidifier chamber that is part of a humidified gases delivery apparatus and system. The method comprising the steps of delivering power to a heater plate, varying the power delivered to the heater plate, measuring the rate of change of temperature and determining the level of water based on the heating characteristics of the volume of water within the chamber, in particular determining the level of water within the chamber based on the rate of change of temperature and the supplied power.

20 Claims, 10 Drawing Sheets

Related U.S. Application Data continuation of application No. 15/261,046, filed on Sep. 9, 2016, now Pat. No. 10,220,177, which is a division of application No. 13/517,405, filed as application No. PCT/NZ2010/000263 on Dec. 23, 2010, now Pat. No. 9,440,042.

(60) Provisional application No. 61/289,512, filed on Dec. 23, 2009.

(51) Int. Cl.

| | | |
|---|---|---|
| *A61M 16/04* | (2006.01) | |
| *A61M 16/06* | (2006.01) | |
| *A61M 16/08* | (2006.01) | |
| *A61M 16/10* | (2006.01) | |
| *A61M 16/12* | (2006.01) | |
| *G01F 23/22* | (2006.01) | |

(52) U.S. Cl.
CPC .......... *A61M 16/024* (2017.08); *A61M 16/04* (2013.01); *A61M 16/0666* (2013.01); *A61M 16/0833* (2014.02); *A61M 16/0875* (2013.01); *A61M 16/104* (2013.01); *A61M 16/109* (2014.02); *A61M 16/1095* (2014.02); *A61M 16/12* (2013.01); *A61M 16/161* (2014.02); *G01F 23/22* (2013.01); *A61M 2016/0039* (2013.01); *A61M 2205/18* (2013.01); *A61M 2205/3368* (2013.01); *A61M 2205/3379* (2013.01); *A61M 2205/3386* (2013.01); *A61M 2205/502* (2013.01); *A61M 2205/52* (2013.01)

(58) Field of Classification Search
CPC .............. A61M 16/021; A61M 16/022; A61M 16/024; A61M 16/026; A61M 16/0833; A61M 16/0841; A61M 16/0875; A61M 16/10; A61M 16/1075; A61M 16/109; A61M 16/1095; A61M 16/16; A61M 16/161; A61M 16/162; A61M 2205/18; A61M 2205/3368; A61M 2205/3379; A61M 2205/3386; A61M 2205/50; A61M 2205/502; A61M 2205/52; F24F 2110/20; G01F 23/22

See application file for complete search history.

(56) References Cited

U.S. PATENT DOCUMENTS

| | | |
|---|---|---|
| 3,860,978 A | 1/1975 | Wirth |
| 3,897,923 A | 8/1975 | Paepke et al. |
| 4,028,444 A | 6/1977 | Brown et al. |
| 4,045,192 A | 8/1977 | Eckstein |
| 4,151,864 A | 5/1979 | Thurman |
| 4,284,878 A | 8/1981 | Bartels |
| 4,441,027 A | 2/1984 | Richardson et al. |
| 4,682,010 A | 7/1987 | Drapeau et al. |
| 4,922,554 A | 5/1990 | Hwang |
| 5,065,785 A | 11/1991 | Deacon et al. |
| 5,346,075 A | 9/1994 | Nichols et al. |
| 5,442,157 A | 8/1995 | Jackson |
| 5,578,000 A | 11/1996 | Greff et al. |
| 5,722,393 A | 3/1998 | Bartel et al. |
| 5,910,291 A | 6/1999 | Skalla |
| 6,050,530 A | 4/2000 | Nakamura |
| 6,095,505 A | 8/2000 | Miller |
| 6,220,245 B1 | 4/2001 | Takebayashi |
| 6,311,936 B1 | 11/2001 | Herr et al. |
| 6,363,930 B1 | 4/2002 | Clawson |
| 6,469,282 B1 | 10/2002 | Roberts |
| 6,523,538 B1 | 2/2003 | Wikefeldt |
| 7,571,744 B2 | 8/2009 | Zia et al. |
| 8,307,825 B1 | 11/2012 | Roberts |
| 8,640,696 B2 | 2/2014 | Pujol |
| 9,440,042 B2 | 9/2016 | McAuley et al. |
| 9,474,512 B2 | 10/2016 | Blackhurst et al. |
| 9,737,675 B2 | 8/2017 | Frame et al. |
| 10,220,177 B2 | 3/2019 | McAuley et al. |
| 10,426,902 B2 | 10/2019 | Blackhurst et al. |
| 11,129,957 B2 | 9/2021 | McAuley et al. |
| 2001/0050080 A1 | 12/2001 | Seakins et al. |
| 2002/0050656 A1 | 5/2002 | Offir et al. |
| 2002/0129815 A1* | 9/2002 | McPhee ................ G01F 1/6888 600/522 |
| 2003/0033848 A1 | 2/2003 | Peng |
| 2003/0034573 A1 | 2/2003 | Mulvaney |
| 2003/0154977 A1 | 8/2003 | White et al. |
| 2003/0183082 A1 | 10/2003 | Schultz et al. |
| 2004/0016430 A1 | 1/2004 | Makinson et al. |
| 2004/0020487 A1* | 2/2004 | Koch .................. A61M 16/164 261/130 |
| 2004/0055597 A1 | 3/2004 | Virr et al. |
| 2004/0079370 A1 | 4/2004 | Gradon et al. |
| 2004/0102731 A1 | 5/2004 | Blackhurst et al. |
| 2004/0221844 A1 | 11/2004 | Hunt et al. |
| 2005/0054993 A1 | 3/2005 | Falahee |
| 2005/0241714 A1 | 11/2005 | Barnhouse et al. |
| 2006/0113690 A1 | 6/2006 | Huddart et al. |
| 2006/0162726 A1 | 7/2006 | Smith et al. |
| 2007/0000908 A1 | 1/2007 | Bohan, Jr. et al. |
| 2007/0137484 A1 | 6/2007 | Roberts |
| 2007/0157929 A1 | 7/2007 | Radomski |
| 2007/0193871 A1 | 8/2007 | Wiseman et al. |
| 2007/0225664 A1 | 9/2007 | Schultz et al. |
| 2007/0272239 A1 | 11/2007 | Aylsworth et al. |
| 2007/0284361 A1 | 12/2007 | Nadjafizadeh et al. |
| 2007/0289449 A1 | 12/2007 | Roberts |
| 2009/0078260 A1 | 3/2009 | Smith et al. |
| 2009/0107493 A1 | 4/2009 | Liu et al. |
| 2009/0110379 A1 | 4/2009 | McGhin et al. |
| 2009/0134282 A1 | 5/2009 | Grim, Sr. |
| 2009/0184832 A1 | 7/2009 | Lloyd et al. |
| 2009/0223514 A1* | 9/2009 | Smith .................. A61M 16/161 128/203.14 |
| 2009/0229606 A1 | 9/2009 | Tang et al. |
| 2010/0043791 A1 | 2/2010 | McAuley et al. |
| 2010/0248176 A1 | 9/2010 | Anderson et al. |
| 2011/0083562 A1 | 4/2011 | Ryan et al. |
| 2011/0147376 A1 | 6/2011 | Ueda et al. |
| 2011/0162647 A1 | 7/2011 | Huby et al. |
| 2011/0253136 A1 | 10/2011 | Sweeney et al. |
| 2016/0375217 A1 | 12/2016 | McAuley et al. |
| 2019/0351157 A1 | 11/2019 | Blackhurst et al. |

FOREIGN PATENT DOCUMENTS

| | | |
|---|---|---|
| GB | 2224957 A | 5/1990 |
| GB | 2460645 A | 12/2009 |
| WO | WO 99/59661 | 11/1999 |
| WO | WO 2006/015416 | 2/2006 |
| WO | WO 2011/078706 | 6/2011 |

\* cited by examiner

HUMIDIFIED GASES DELIVERY APPARATUS AND METHODS FOR CONTROLLING SAME

CROSS-REFERENCE TO RELATED APPLICATIONS

This application is a continuation of U.S. patent application Ser. No. 16/252,339, filed Jan. 18, 2019, now U.S. Pat. No. 11,129,957, which is a continuation of U.S. patent application Ser. No. 15/261,046, filed on Sep. 9, 2016, now U.S. Pat. No. 10,220,177, which is a divisional of U.S. patent application Ser. No. 13/517,405, filed on Mar. 28, 2013, now U.S. Pat. No. 9,440,042, which is a National Phase of International Application No. PCT/NZ2010/000263, filed Dec. 23, 2010, which claims priority from U.S. Provisional Application No. 61/289,512, filed Dec. 23, 2009.

BACKGROUND OF THE INVENTION

Field of the Invention

This invention relates to a humidified gases delivery apparatus and methods for controlling same.

Description of the Related Art

A number of methods and systems are known in the art for assisting a patient's breathing. Continuous Positive Airway Pressure (CPAP) involves administration of air under pressure to a patient, usually by a patient interface like a mask. CPAP is usually used to treat snoring and Obstructive Sleep Apnea (OSA). More complete breathing support is provided by a ventilator.

There are problems associated with air delivery to the airways of patient's. Mucosal drying is one such problem. Mucosal drying is uncomfortable and may awaken patients during the night. Rebound nasal congestion commonly occurs during the following day, simulating a viral infection.

Such symptoms can also occur in a hospital environment when patients are on a respirator. Typically patients in this situation are intubated but alternatively air may be delivered to the patient via other patient interfaces like masks or nasal cannula. Patients in the hospital environment can also suffer from mucosal drying, rebound nasal congestion and also from dryness, irritation and inflammation of the throat due to intubation. These problems all cause distress to the patient and may lead to further respiratory problems.

A number of methods have been employed to combat the symptoms and conditions described earlier. Some of the methods involve pharmacologic agents to reduce nasal disease or heating the patient's room. The most commonly employed method is humidification of the gases delivered to the patient. The humidified gases go some way to reducing or minimising the problems caused by air or gases delivery to a patient. Humidifiers and methods of humidifying breathing gases are known in the art. Most common humidification methods employ a humidification chamber including a reservoir of water and heater plate. The water is heated to create water vapour and gases are passed through the humidification chamber. The gases collect and hold the water vapour and are hence humidified. The humidification chamber can only hold a finite amount of water and needs to be refilled by the user or by a hospital worker in a hospital environment. Accordingly the user or health professional needs to monitor the water level within the chamber and add more water when required. This can be a tedious task and can be overlooked. A level sensor connected within the chamber is one way to measure the level of water within the humidification chamber. This is too difficult to implement and can be cumbersome. The level sensor is difficult to implement because it requires electrical connections within the humidification chamber, the sensor requires calibration and the sensor can interfere with the humidification of gases.

US 2008/0142019 discloses a high flow therapy system including a non sealing respiratory interface with a sensor disposed near it. The system also includes a humidification chamber to humidify gases and a heater plate to heat the contents of the humidification chamber. The system includes a microprocessor to control the heater plate and measure the pressure of gases delivered. The document discloses monitoring temperature and power data of the heater plate to determine the status of the water level in the humidity chamber and can trigger automatic refill of the chamber.

US 2002/0112725 discloses a breathing assistance apparatus for delivering humidified gases to a patient. The system includes a humidification chamber with a heater plate and a microprocessor to control the heating of the heater plate. The document discloses a method of determining the amount of power required to heat the contents of the humidifier to the appropriate temperature such that the gases are humidified to their correct level.

US 2004/0079370 discloses a flow probe for use in a humidification system. The probe provides temperature and flow rate sensing. The document discloses a "water out alarm" that warns a user when the level of water within the humidification chamber is too low. The system calculates thermal conductivity based on the heater plate power requirement, heater plate temperature and chamber temperature. The controller compares this calculated thermal conductivity with a threshold value. If the threshold value is greater than the thermal conductivity then the level of water is too low.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is an object of the invention to provide a method of control that may go some way to overcome or to at least provide the public with a useful alternative.

Accordingly in a first aspect the invention may be said to broadly consist of a method of determining the water level in a humidifier chamber within a humidified gases delivery system, said method comprising the steps of: delivering power to a heater used to heat the contents of the chamber, determining a temperature increase over a time period while the power is delivered, determining a level of water within the chamber based the delivered power, the temperature increase and the time period.

Preferably the level of water within the chamber is determined based on the rate of temperature increase and the delivered power.

Preferably the level of water within the chamber is determined from a look up table, the look up table storing values relating the temperature change over a set time period, for a given power with the level of water within the chamber.

Alternatively the level of water within the chamber is determined by using an equation for heat energy into a substance and rearranging the equation to solve for the mass.

Preferably said method includes the additional steps of measuring temperature of the chamber contents prior at start up, measuring temperature after said time period has elapsed, determining temperature increase based on a difference between final temperature and initial temperature.

Preferably the method described earlier is used to determine the initial level of water within the chamber at the beginning of therapy.

In another aspect the invention can be said to broadly consist in a method of determining the water level in a chamber within a humidified gases delivery system wherein the method includes the steps of: delivering power to a heater to heat the contents of the chamber, reducing power to the heater for a period of time, determining a temperature drop over a set period of time while the heater is supplied a reduced power, determining a level of water within the chamber based on the reduced power, the temperature drop and the period of time.

Preferably the level of water within the chamber is determined based on the rate of temperature decrease.

Preferably said method includes the additional steps of measuring the temperature of the chamber contents prior to reducing the power, measuring temperature after the period of time of reduced heater plate power.

Preferably the level of water within the chamber is determined from a look up table, the look up table containing the relationship between temperature drop and level of water within the chamber.

Preferably the method described is used to determine the level of water within the chamber at the start of therapy or during therapy.

In a further aspect the invention can be said to consist in a method of delivering humidified gases to a patient by a humidified gases delivery system comprising the steps of: determining water level in a chamber within said humidified gases delivery system as per any one of the statements above, receiving and storing a patient's treatment data including at least the average treatment time, controlling the power supplied to a heater plate such that amount of water in said chamber lasts for at least a substantial part of the treatment time while providing a minimum amount of humidification as per said patient's treatment data.

Preferably any one of the methods described earlier may further comprise the steps of: measuring the level of water in the chamber prior to beginning treatment, alerting a user if the level of water is too low prior to the start of treatment or during the early stages of treatment.

Alternatively any one of the methods described earlier further comprising the steps of: determining the level of water in the chamber during treatment of the patient, switching off power to the heater plate if the water level in the chamber is below a minimum water level.

Preferably the level of water within the chamber is determined based on the rate of temperature increase and the delivered power.

Alternatively the level of water within the chamber is determined based on the rate of temperature decrease when power to the heater is either switched off or reduced.

Alternatively the level of water within the chamber is determined by any one of the methods described earlier.

In a further aspect the invention can be said to consist in a humidification apparatus adapted to humidify a stream of gases, the humidification apparatus comprising: a humidification chamber, the humidification chamber adapted to hold a volume of water, the humidification chamber including an inlet for receiving a stream of gases and an outlet, a heater plate, in use, in contact with the humidification chamber, the heater plate adapted to heat the humidification chamber and contents within the chamber to create water vapour within the chamber, an electronic controller adapted to control the power supplied to the heater plate, the controller adapted to: deliver power to a heater used to heat the contents of the chamber, determine a temperature increase over a time period while the power is delivered, determine a level of water within the chamber based the delivered power, the temperature increase and the time period.

In a further aspect the invention can be said to consist in a humidification apparatus adapted to humidify a stream of gases, the humidification apparatus comprising: a humidification chamber, the humidification chamber adapted to hold a volume of water, the humidification chamber including an inlet for receiving a stream of gases and an outlet, a heater plate, in use, in contact with the humidification chamber, the heater plate adapted to heat the humidification chamber and contents within the chamber to create water vapour within the chamber, an electronic controller adapted to control the power supplied to the heater plate, the controller adapted to: deliver power to a heater to heat the contents of the chamber, reduce the power to the heater for a period of time, determine a temperature drop over a set period of time while the heater is supplied a reduced power, determine a level of water within the chamber based on the reduced power, the temperature drop and the period of time.

In a further aspect the invention can be said to consist in a humidification apparatus adapted to humidify a stream of gases, the humidification apparatus comprising: a humidification chamber, the humidification chamber adapted to hold a volume of water, the humidification chamber including an inlet for receiving a stream of gases and an outlet, a heater plate, in use, in contact with the humidification chamber, the heater plate adapted to heat the humidification chamber and contents within the chamber to create water vapour within the chamber, an electronic controller adapted to control the power supplied to the heater plate, the controller adapted to: determine water level in a chamber within said humidified gases delivery system, receive and storing a patient's treatment data including at least the average treatment time, control the power supplied to a heater plate such that amount of water in said chamber lasts for at least a substantial part of the treatment time while providing a minimum amount of humidification as per said patient's treatment data.

In another aspect the invention can be said to broadly consist in a humidified gases delivery system for delivering humidified gases to a patient comprising: a pressurised gases source, a humidification chamber, the humidification chamber adapted to hold a volume of water within it, the humidification chamber having an inlet and outlet, the humidification chamber receiving a stream of gases from the gases source through the inlet, the stream of gases being humidified within the chamber and exiting through the outlet, a heater plate adapted to heat the contents of the humidification chamber, a patient interface receiving humidified gases from the humidification chamber and delivering the humidified gases to the patient, a controller regulating the power delivered to the heater plate and flow rate of the gases source, the controller adapted to implement any one or all of the methods described earlier.

ALTERNATIVE EMBODIMENTS

Other alternative embodiments can include any one or any combination of the following methods.

One alternate embodiment could include a method of determining the water level in a chamber within a humidified gases delivery system upon start up of the system, the method comprising the steps of: delivering power to a heater used to heat the contents of the chamber, measuring the time for the chamber contents to reach a target temperature, determining level of water within the chamber based on amount of time it takes for the chamber contents to reach a target temperature.

Preferably the level of water within the chamber is determined from a look up table, the look up table containing the relationship between time taken to reach a target temperature and level of water within the chamber.

Preferably said method includes the steps of measuring temperature prior to heating and measuring temperature throughout said heating period to monitor when target temperature is reached.

Another alternate embodiment could include a method of determining the water level in a chamber within a humidified gases delivery system upon start up of the system as claimed in any one of the preceding claims, the method comprising the further steps of: delivering a power to a heater used to heat the contents of the chamber, measuring initial temperature, reducing the power delivered to the heater, measuring the time taken for chamber contents to reach a target temperature while a reduced power is delivered, determining level of water within the chamber based on the time taken to reach a target temperature and the reduced power level.

Preferably the level of water within the chamber is determined from a lookup table, the lookup table relating the level of water within the chamber with time to reach a target temperature.

Another alternate embodiment could include a method of determining the water level in a chamber within a humidified gases delivery system in use, the method comprising the steps of: delivering power to a heater plate to heat the contents of the chamber, measuring initial temperature of the chamber contents, changing the amount of power to a heater plate for a time period to cause a change in temperature of the water within the chamber, determining the change in temperature over a set time period once the power to the heater plate is varied, calculating the level of water within the chamber based on a relationship between the change in temperature, time period and delivered power.

Preferably said power to the heater plate is switched off over a set period of time order to determine the level of water within the chamber based on relationship between change in temperature and time period.

Preferably said power is increased over said set time period, said water level is determined based on change in temperature, power delivered and time period.

Preferably the method includes measuring the ambient air temperature and air flow rate before determining the level of water within the chamber.

Preferably the method described is performed at set time intervals and the calculated water level stored each time the method is performed.

Preferably the method includes storing the value of water level calculated in the previous time interval, calculating evaporation rate of water from the chamber, and calculating actual level of water within the chamber by subtracting the evaporation rate from the water level for the previous time interval.

Preferably the initial water level value is received by the controller as a user input from a user interface.

Alternatively the initial water level value can be measured by an appropriate sensor.

Another alternate embodiment could include a method of determining ambient humidity, the method comprising the steps of: determining changes in an amount of water in a chamber, measuring air flow rate into the chamber, measuring ambient temperature, determining the ambient humidity based on the change in water level, the air flow, and ambient temperature.

Preferably the method comprising the step of calculating ambient humidity from a look up table relating water level in a humidification chamber, ambient temperature, air flow rate and ambient humidity.

Another alternate embodiment could include a method of determining the water level in a chamber within a humidified gases delivery system in use, the method comprising the steps of: measuring temperature of chamber contents, determining change in temperature over a first set period of time once the power to the heater plate is varied, calculating water level for said set time period and delivered power storing value.

Another alternate embodiment could include a method determining water level in a chamber within a humidified gases delivery system comprising the steps of: receiving a water level value from a user input, storing said water level value, calculating an evaporation rate of water from said chamber, calculating actual value of water level within chamber by subtracting said calculates evaporation rate from the stored water level value.

Preferably method is repeated in use at specified time intervals.

Another alternate embodiment could include a method of determining water level in a chamber within a humidified gases delivery system in use, the method comprising the steps of: receiving an initial water level value from a user input via a user interface, storing an initial water level value, measuring temperature of chamber contents, delivering power to a heater plate to cause a change in temperature of water within said chamber, determining change in temperature over a set time period as power level to the heater plate is varied, determining an evaporation rate of water from said chamber, calculating a level of water based on the initial water level, evaporation rate, change in temperature, time period and power level delivered.

Preferably said method includes measuring the ambient temperature and air flow rate before determining the level of water within the chamber.

Preferably said evaporation rate is calculated based on mass transfer of gases through said chamber, wet surface area, wet surface vapour pressure and vapour pressure of gases flow.

Preferably said wet surface area is determined based on the geometry of said chamber, said wet surface area value is calculated, stored in memory before calculating evaporation rate, the wet surface area is called from memory to calculate evaporation rate.

Preferably the mass transfer is calculated based on universal gases constant, molecular mass of gases and the mass transfer coefficient, the mass transfer value is calculated and stored in memory before calculating evaporation rate and called from memory to calculate evaporation rate.

Preferably said method includes the steps of measuring ambient humidity, volume flow rate of gases and vapour pressure for said gases flow into said chamber before determining the evaporation rate of water from the chamber.

Preferably said wet surface vapour pressure is determined based on ambient humidity and said mass transfer coefficient is calculated based on said volume flow rate and flow pattern behaviour, and the wet surface vapour pressure and mass transfer coefficient is calculated before determining the evaporation rate.

Preferably any one of the previously described methods further comprises the steps of: controlling the power supplied to said heater plate such that amount of water in said chamber lasts for at least a substantial part of the treatment time while providing an adequate amount of humidification for a nominal treatment time.

Preferably said nominal treatment time is based on a historical record of patient treatment times.

Preferably any one of the methods described earlier may further comprise the step of: receiving and storing a patient's treatment data in particular the average treatment time for a patient and the required amount of humidification.

Another alternate embodiment could include a method of determining the water level in a humidifier chamber at start up which is being used as part of a humidified gases delivery system upon start up of said system, said system including a heater which in use is used to heat the contents of said humidifier chamber, a temperature sensor to measure the temperature of the contents of said humidifier chamber, and a controller which receives data from said temperature sensor, said method comprising the steps of: measuring the temperature of the contents of said chamber, delivering power at a known rate to said heater, measuring the temperature of the contents of said chamber after a period of time has passes an determining the temperature increase of said contents over said time period, determining a level of water within said chamber based on the amount of power delivered, said temperature increase and said time period.

Another alternate embodiment could include a method of determining the water level in a humidifier chamber which is being used as part of a humidified gases delivery system upon start up of said system, said system including a heater which in use is used to heat the contents of said humidifier chamber, a temperature sensor to measure the temperature of the contents of said humidifier chamber, and a controller which receives data from said temperature sensor, said method comprising the steps of: delivering power to a heater to heat the contents of the chamber, reducing power to the heater for a period of time, determining a temperature drop over a set period of time while the heater is supplied a reduced power, determining a level of water within the chamber based on the reduced power, the temperature drop and the period of time.

Another alternate embodiment could include a method of determining the water level in a humidifier chamber at start up which is being used as part of a humidified gases delivery system upon start up of said system, said system including a heater which in use is used to heat the contents of said humidifier chamber, a temperature sensor to measure the temperature of the contents of said humidifier chamber, and a controller which receives data from said temperature sensor, said method comprising the steps of: delivering power to a heater used to heat the contents of the chamber, measuring the time for the chamber contents to reach a target temperature, determining level of water within the chamber based on amount of time it takes for the chamber contents to reach a target temperature.

Another alternate embodiment could include a method of determining the water level in a humidifier chamber at start up which is being used as part of a humidified gases delivery system during operation or use of said system, said system including a heater which in use is used to heat the contents of said humidifier chamber, a temperature sensor to measure the temperature of the contents of said humidifier chamber, and a controller which receives data from said temperature sensor, said method comprising the steps of: delivering power to a heater plate to heat the contents of the chamber, measuring initial temperature of the chamber contents, changing the amount of power to a heater plate for a time period to cause a change in temperature of the water within the chamber, determining the change in temperature over a set time period once the power to the heater plate is varied, calculating the level of water within the chamber based on a relationship between the change in temperature, time period and delivered power.

Another alternate embodiment could include a method of determining the water level in a humidifier chamber at start up which is being used as part of a humidified gases delivery system during operation or use of said system, said system including a heater which in use is used to heat the contents of said humidifier chamber, a temperature sensor to measure the temperature of the contents of said humidifier chamber, and a controller which receives data from said temperature sensor, said method comprising the steps of: measuring temperature of chamber contents, determining change in temperature over a first set period of time once the power to the heater plate is varied, calculating water level for said set time period and delivered power storing value.

Another alternate embodiment could include a method of determining the water level in a humidifier chamber at start up which is being used as part of a humidified gases delivery system during operation or use of said system, said system including a heater which in use is used to heat the contents of said humidifier chamber, a temperature sensor to measure the temperature of the contents of said humidifier chamber, and a controller which receives data from said temperature sensor, said method comprising the steps of: receiving an initial water level value from a user input via a user interface, storing an initial water level value, measuring temperature of chamber contents, delivering power to a heater plate to cause a change in temperature of water within said chamber, determining change in temperature over a set time period as power level to the heater plate is varied, determining an evaporation rate of water from said chamber, calculating a level of water based on the initial water level, evaporation rate, change in temperature, time period and power level delivered.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth. The invention consists in the foregoing and also envisages constructions of which the following gives examples only The term "comprising" as used in the specification means "consisting at in part of". When interpreting each statement in this specification that includes the term "comprising", features other than that or those prefaced by the term may

DETAILED DESCRIPTION OF THE PREFERRED EMBODIMENT

Humidification System

Figure 1:
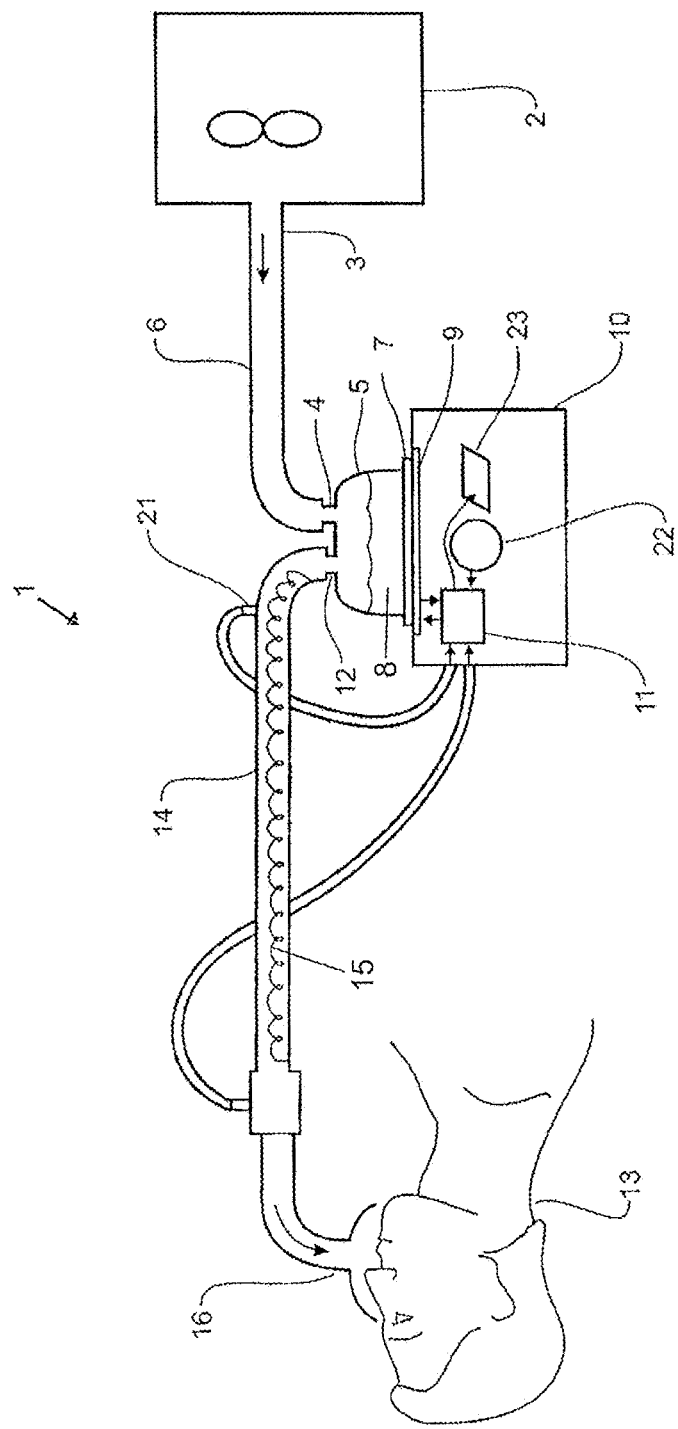
FIG. 1 shows a ventilator humidification system for delivering humidified breathing gases to a user.
Figure 2:
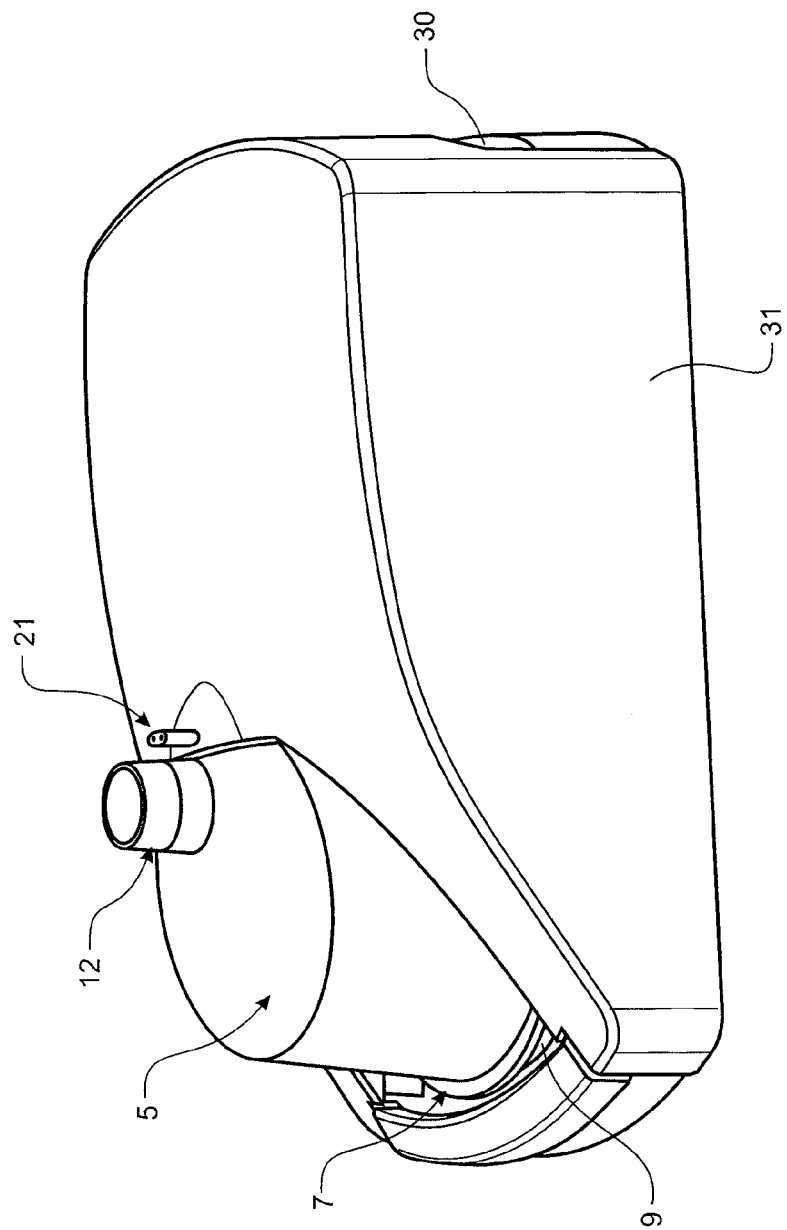
FIG. 2 shows a CPAP humidification system for use as part of a system for delivering humidified breathing gases to a user.

With reference to the drawings, example humidification apparatus or respiratory humidification systems, incorporating the present invention are illustrated. FIG. 1 shows a respiratory humidification system 1 including a ventilator or gases supply means or a ventilator 2 having an outlet 3 which supplies gases (for example air, oxygen, anaesthetic gases) to the inlet 4 of a humidification chamber 5. In a ventilator system the inlet of the humidifier chamber 5 is connected to the outlet of the ventilator 2 by a suitable conduit 6. FIG. 2 shows a typical CPAP system where the humidifier is integrated with a blower 30 for drawing in ambient air and delivering it under pressure to the humidifier chamber 5. The blower and humidification chamber 5 are integrated in one unit. The blower is situated in housing 31.

The humidification chamber 5 may, for example, comprise a plastics formed chamber having a heat conductive base 7, the base sealing the bottom of the chamber 5. The humidification chamber 5 is adapted to hold a volume of water 8 within it and the base 7 of the humidification chamber is preferably formed from a heat conductive material such as aluminium. The heat conductive base 7 of the chamber 5 is in contact with a heater plate 9 of a humidification device or humidifier 10. The humidifier 10 includes a controller 11. The controller controls the operation of the heater plate 9 and also controls other parts and features of the humidification system.

As the water within the chamber 5 is heated it will slowly evaporate, mixing water vapour with the gases flow through the humidification chamber 5 from the blower 2. Accordingly, the humidified gases leave the chamber 5 via the outlet 12 of the chamber and are delivered to a patient 13 or other person in need of such gases through a gases transportation pathway or inspiratory conduit 14. In order to reduce condensation within the inspiratory conduit 14 and to raise the temperature of the gases provided to the patient 13, a heating wire 15 may be provided within, around or adjacent the inspiratory conduit 14. The heating wire may be energised by a current supplied from the humidifier 10. The supply of current may be controlled by the controller 11.

FIG. 1 shows a patient interface 16. In this example the interface is a mask over the patient's nose and mouth. Many other patient interfaces such as nasal cannula, nasal pillows, nasal mask, oral mask, intubation, full face masks, nasal puffs and oro-nasal masks may be used to deliver humidified and pressurised gases to a patient. The patient interface 16 is connected to the inspiratory conduit 14 and adapted to receive gases from the inspiratory conduit 14 and deliver the gases to the nasal passages or oral passage of the patient 13. It is also possible to provide a return path for the patient's exhaled gases back to the blower or ventilator 2. In this case a suitable fitting such as a "Y piece" may be attached between the patient 13, the inspiratory conduit 14 and an expiratory conduit (not shown) which is connected to an inlet (not shown) of the ventilator or blower 2.

The controller 11 may for example comprise a microprocessor or logic circuit with associated memory or storage which holds a software programme. The software program preferably includes a set of instructions regarding the operation and control of the system 1. The software programme is executed by the controller to control the operation of the system based on the instructions in the software programme and based on external inputs. The controller implements methods of determining the water level in the humidification chamber 5. These methods and other functions of the controller will now be described in more detail.

In an alternate form the CPAP device or respiratory humidification system may include a user interface 22. The user interface allows a user to communicate with the controller. The user interface also allows the controller 11 to communicate information regarding the system or CPAP device to the user. In the most preferred form the user interface includes a screen and a keypad. The user can input information from the keypad. The keypad is connected to the controller and feeds user information into controller 11. The information from the keypad is transmitted in the appropriate format to allow the controller 11 to process the information or alternatively the controller may convert the information from the keypad into the correct format. The screen outputs information from the controller 11 to the user. The screen is preferably an LCD screen but alternatively could be any other screen to display information. The screen preferably is adapted to display information in alphanumeric format but may display information in any other suitable format. The keypad and screen may also be in communication with other elements of the respiratory humidification system or CPAP device.

Figure 7:
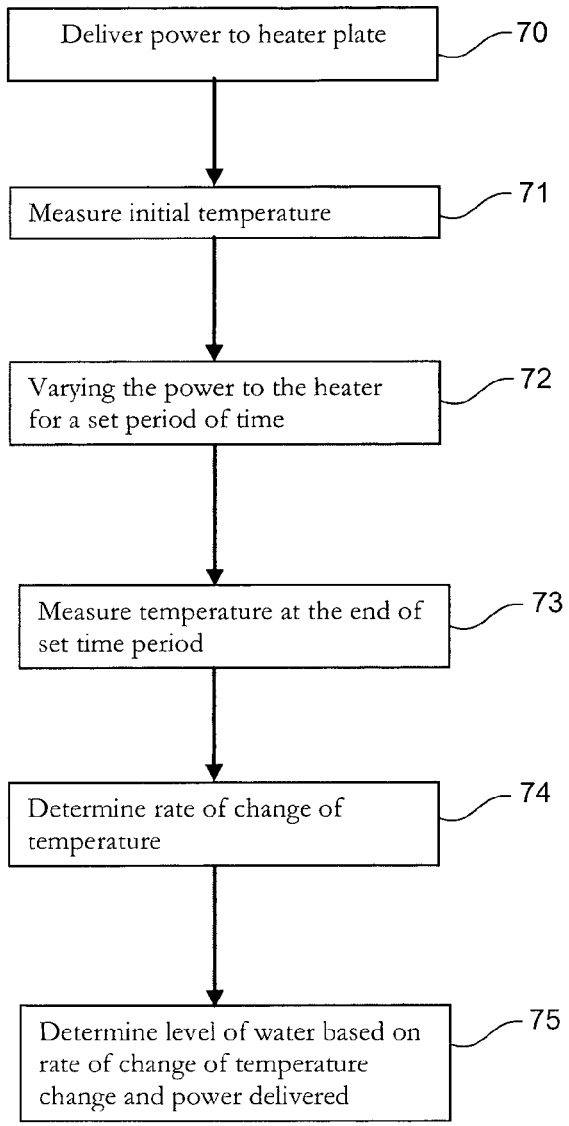
FIG. 7 shows a flow chart of a generalised method for determining the level of water in a humidifier chamber in use, based on the change in temperature.

FIG. 7 shows the generalised method of determining water level in a humidifier chamber. The method is preferably implemented by a controller 11. The method starts by delivering power to a heater plate at step 70. The controller determines the power level delivered to a heater plate and is constantly delivering power when the system 1 is providing humidified gases. The initial temperature of the water in the chamber 5 is then measured at step 71. The controller determines initial temperature of the water using a sensor. The controller receives the information from the sensor. This step is optional and does not need to be performed; however in most cases this step will be performed. Next the power to the heater is varied for a set period of time at step 72. The controller 11 can either increase the power or decrease the power or switch off the power delivered to the heater plate 9. Next the temperature at the end of the set time period is measured at step 73. The controller measures the temperature at the end of the time period for which the power level was varied. Next the rate of change of temperature is determined at 74. The rate of change of temperature is the temperature response of the particular volume of water. Although the method states the power is varied for a set period of time, as an alternate the power may be varied until a set temperature is reached and the time taken to reach the set temperature can be measured. The temperature response (rate of change of temperature) is the change in temperature over change in time. The method can measure temperature change for a known time or alternatively measure the time taken for a set temperature change to occur. Both of these ways to determine rate of change of temperature is part of the present invention. Next the level of water based on rate of change of temperature and the power delivered is determined at step 75. The controller determines the level of water within the chamber based on the temperature response for a particular power level or change in power level. The relationship between the rate of change of temperature and power level to water level can be determined from a look table or a derived equation for the system. The look up table is constructed and the relationship of water level to rate of change of temperature (temperature response) is determined experimentally by measuring and storing various temperature responses for various volumes of water in the chamber.

Chamber Water Level at Start Up

Figure 4:
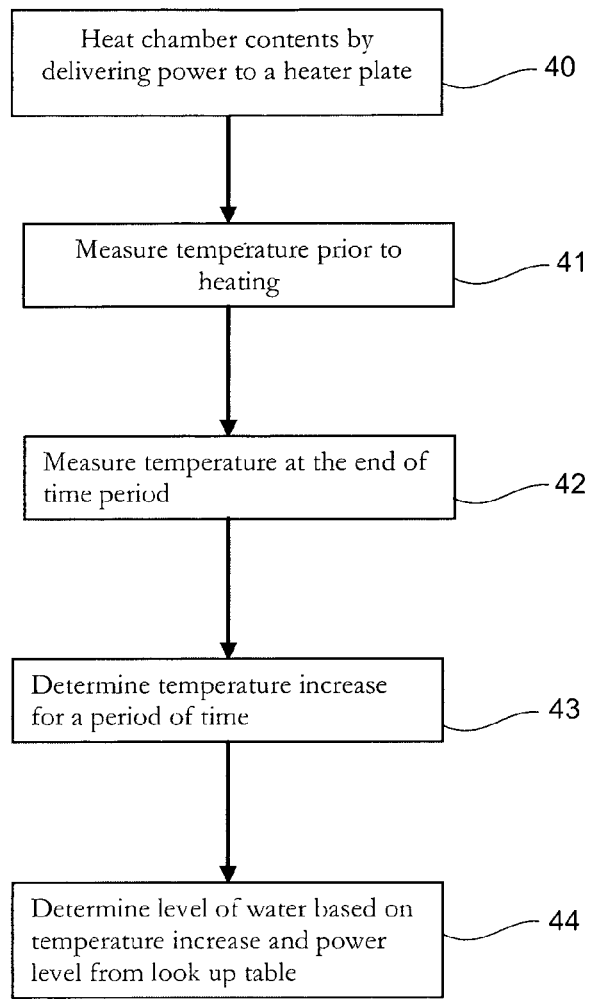
FIG. 4 shows a flow chart of a method for determining level of water in a humidifier chamber based on temperature increase over a period of time.
Figure 5:
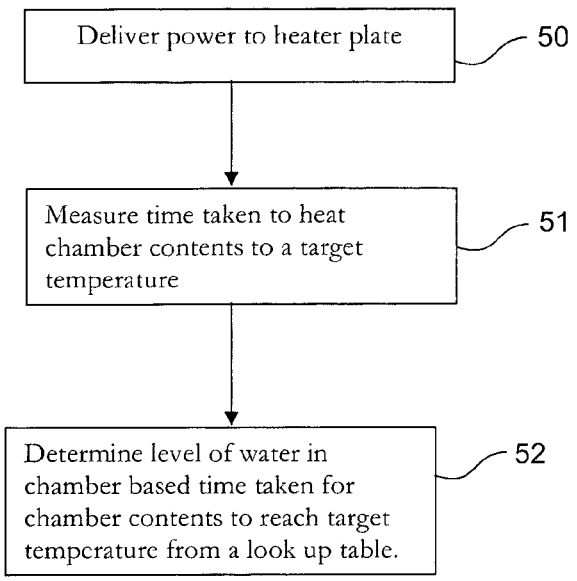
FIG. 5 shows a flow chart of a method for determining level of water in a humidifier chamber based on time taken to heat the chamber contents to a target temperature.

FIGS. 4 and 5 show a flow chart of steps to determine the level of water at start up of the chamber. The chamber water level is measured by the controller 11 on start up of the system to determine a base amount of water in the humidification chamber 5. At start up the controller 11 delivers power to the heater to heat the chamber contents at step 40, or step 50. Preferably the controller 11 energises the heater plate 9 to its full power and measures time taken for the chamber contents to reach a percentage of a predetermined temperature or reach the predetermined temperature at step 50. At step 43 also the rate of change of temperature may be determined as the time taken to reach a target temperature for a given power input. For example, at full power the controller measures the time the chamber contents take to reach 75% of a predetermined temperature. More specifically at step 41 the controller determines the initial temperature prior to heating. At step 42 the temperature after heating is measured or the temperature is measured to determine if a target temperature is reached. Once the time is measured the controller throttles down the power supplied to the heater plate to a lower power value. The heater plate power input may be stepped to heat the water within the chamber 5 at various temperatures and measure the temperature response of the water in order to determine the water level within the chamber 5. At step 43 the rate of change of temperature is measured. More specifically at start up (in step 43) the temperature increase over a period of time is determined. The temperature of the chamber can be determined by either measuring the temperature of the water, the wall of the chamber, the heater plate or the outlet air temperature at the chamber outlet. The controller relates the time taken to heat the water to a predetermined temperature with the thermal mass of the water in the chamber 5. The system may measure the initial temperature of the water or ambient temperature of the water using a sensor or any other suitable means. The change in temperature is calculated by using the initial temperature of the water and the final measured temperature of the water. The temperature response or rate of change of temperature can be determined by the controller 11.

Preferably the controller 11 accesses a look up table that relates the rate of change in temperature with the level of water within the chamber for a given heat energy input at step 44 or step 52. The look up table preferably comprises the rate of change of temperature with a corresponding water level value for a particular heat or electrical power input. The look up table includes the rate of change of temperature or temperature values and a corresponding water level values for a range of electrical power or heat supplied to the heater plate. Preferably the look up table is stored in memory of the humidification device 10. The memory is also associated with the controller 11, which can access the memory for reading information from the memory and writing information to the memory. The controller 11 uses the look up table to determine the level of water within the chamber based on the look up table that relates the rate of change of temperature and water level at different power levels. In an alternate form the look up table may relate the amount of temperature change with the level of water within the chamber 5. For example the level of water can be related to the amount of temperature change over a selected time period instead of the rate of change of temperature at a given power level. The look up tables may be created based on experimental results of various rates of temperature change for various volumes of water at various ambient conditions.

Figure 13:
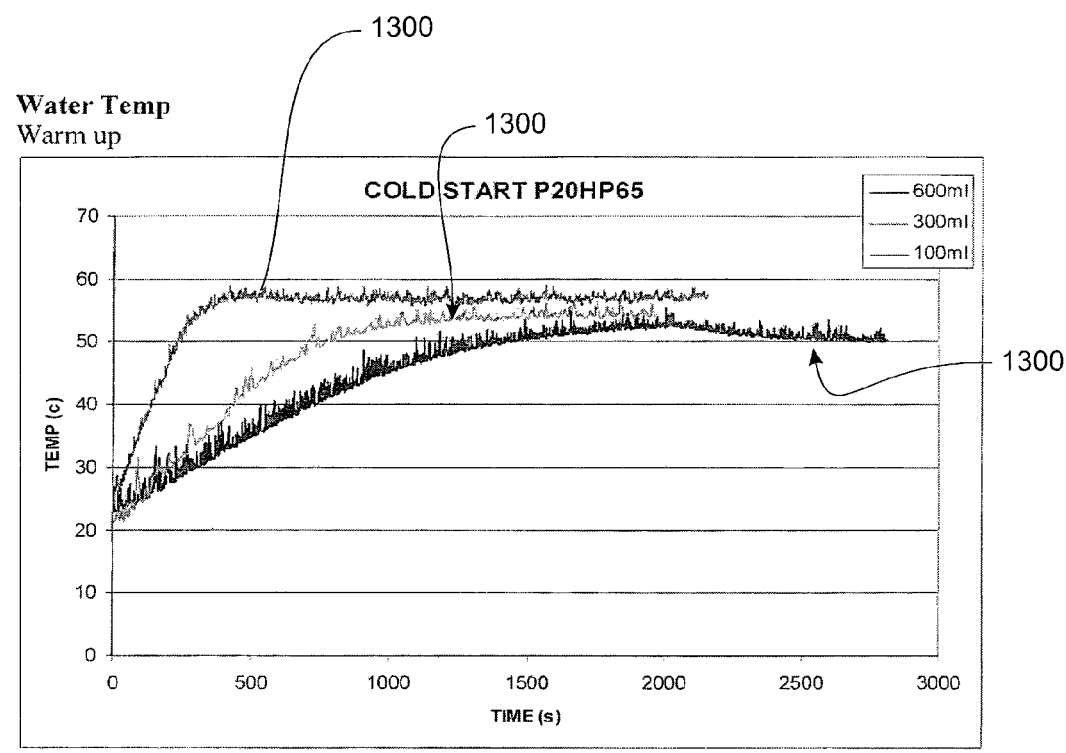
FIG. 13 shows the temperature response for heating the water until a steady state temperature is reached.

FIG. 13 shows an experimental plot of temperature response for various water levels. This could form the basis of a lookup table. FIG. 13 is a plot of temperature response at 85 Watts delivered to the heater plate 9. Preferably the lookup table is based on the data from several plots like the one in FIG. 13, each of these plots being for a different power level supplied to the heater. The plot in FIG. 13 shows the temperature increasing as power is delivered because this is the plot at start up. For clarity FIG. 13 shows three temperature response curves relating to 3 water levels. The system preferably includes measured or plotted temperature responses for several volumes. Most preferably the temperature response is measured or experimentally determined for all operational volumes or levels of water. Operational volumes or operational levels of water means the various water levels or volumes that are required during humidification. For example the minimum volume of chamber may be 10 ml and the maximum operational volume may be 800 ml. The temperature responses are determined or resolved for every volume in this case at 100 ml, 300 ml and 600 ml. This is one example, but the temperature responses could be for any interval of volumes of water for clarity only 3 volumes are shown in FIG. 13 but more generally more volumes could be plotted, e.g. at 2 ml intervals from 10 ml to 800 ml. The water level in the chamber for 85 Watts can be found by determining or measuring the temperature after an interval of time and referring to the graph for the water level. In one alternate form the rate of change of temperature can be measured between the initial temperature and up to a leg 1300 in the graph. The temperature is a steady state temperature after the leg, as per FIG. 13. The steady state temperature may be reached for particular power levels or the heater is switched off once the temperature rate of change is determined, the switched off heater could be denoted by the leg 1300. Graphs or lookup tables could be generated for correlating water levels to other power input levels also. FIG. 13 is one example for 85 Watts. FIG. 13 shows the temperature response for the water within the chamber.

Alternatively the look up table may include an embedded formula that relates the rate of change of temperature, or the time taken for the temperature to reach a predetermined temperature and the level of water for various ambient conditions and flow rates. The controller runs the formula on sensor inputs of ambient conditions, temperature values or temperature rate of change, flow rates and time periods of heating and cooling. The embedded formula may be stored in the controller memory. The formula may be worked out and programmed into the controller.

Alternatively the controller may calculate the water level in the chamber using the equation for thermal mass of the water. Thermal mass is equal to the amount of water multiplied by its specific heat capacity. The specific heat capacity of water is a known value that can be programmed into the controller and stored in the memory associated with the controller 9. The equation for heat energy put into or taken out of a volume of material is based on the thermal mass multiplied by the change in temperature. The amount of heat energy is expressed by the equation below $$Q = mc\Delta T$$

Q=Heat energy supplied to a substance
m=Mass
c=Specific heat capacity
$\Delta T$=Change in temperature.

The heat energy supplied to the volume of water in the chamber is known since it is related to the energy supplied to the heater plate. The heater plate is energized to full power meaning the heat energy Q is equal to the maximum electrical power supplied to the heater plate minus any losses within the heating system and/or the heater plate. At start up the contents of the chamber are heated until a set temperature is achieved or alternatively the contents of the chamber 5 are heated for a set period of time and the change in temperature is measured. Based on the equation for heat applied to the contents of the chamber 5 (shown above), the mass of the water within the chamber can be calculated. The volume of water can be calculated from the mass of the water.

In a further preferred form of the method of water level measurement the controller measures a drop in temperature with power received from the heater plate 9. This method has the advantage that it is independent of manufacturing variations like the heater plate heating characteristics which may vary from unit to unit or thermal conductivity through the heater plate. In the most preferred form the water in chamber 5 is heated to a known temperature and the heater plate is energised to a set power level. The controller then measures the time for the chamber or chamber contents to drop in temperature from a first known temperature to a second known temperature. For example the chamber contents are heated to 40 degrees Celsius and then the time is measured for the chamber contents to drop from 40 degrees Celsius to 30 degrees Celsius. Alternatively the controller may measure the drop in temperature over a set time; this set time may be stored in the controller memory. The level of water within the chamber is determined using a look table that relates the temperature drop with the water level within the chamber. The relationship between temperature drop and water level is determined experimentally and stored into the memory associated with the controller. The basic relationship between water level and temperature drop is; larger the water mass or volume the longer it takes for the temperature to drop. A larger volume or mass of the water results in a longer cool down period.

In a further alternate form the user can input the initial water level value through the user interface. The controller may store this initial water level value or may display it back to the user. The controller may also ask the user conformation of the water level value through the screen.

Chamber Water Level During Use

Figure 3:
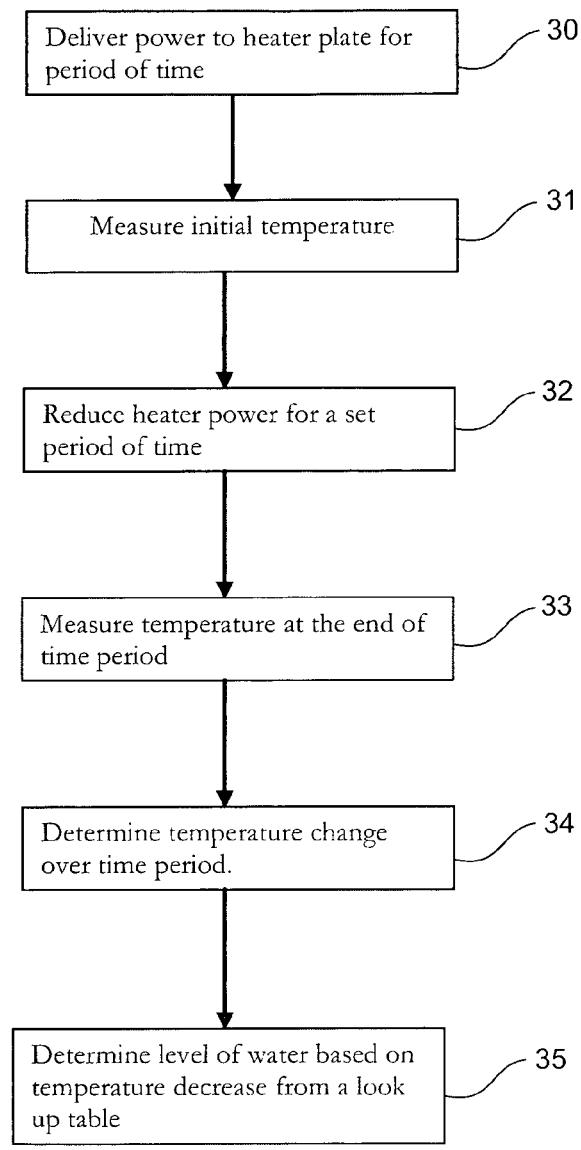
FIG. 3 shows a flow chart of a method for determining level of water in a humidifier chamber based on cooling over a period of time.
Figure 6:
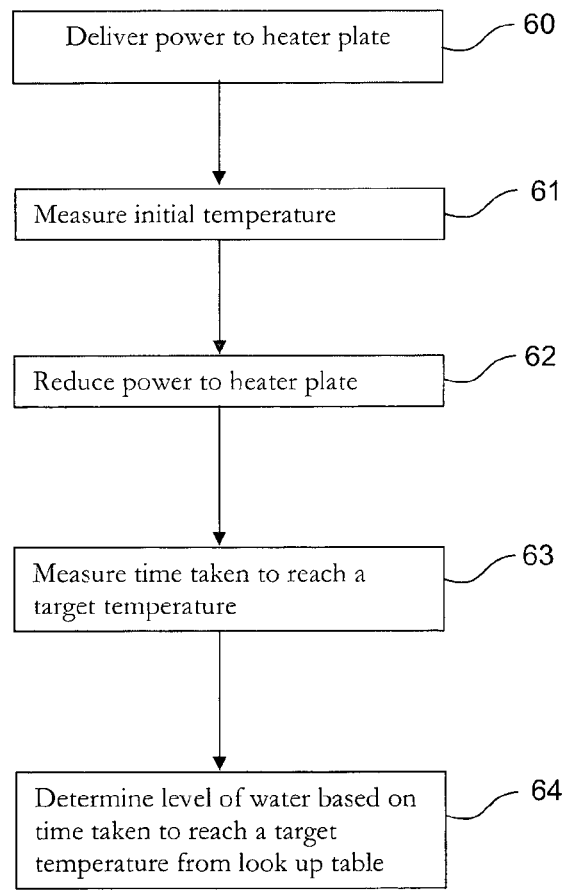
FIG. 6 shows a method for determining level of water in a humidifier chamber based on time taken for the chamber contents to cool to a target temperature.

FIGS. 3 and 6 show a flow chart for determining the level of water based on the cooling rate of change for a level of water. The flow charts show methods that can be used to determine level of water in a chamber 5 during use. The controller 9 can also calculate the amount of water in the chamber while the chamber 5 is in use by running a second method described below. In use respiratory or breathing gases flow into the chamber 5 through the chamber inlet, become humidified and flow out of the chamber outlet. At step 30 or step 60 the controller delivers power to the heater plate. This is the in use condition where the heater plate is energised to heat the water such that water vapour is created to humidify the gases flow. At step 31 or step 61 the controller measures the initial temperature. The controller 11 varies the power provided to the heater plate at step 62 or step 32. Preferably the controller reduces the power to the heater plate and even more preferably the controller switches off the power to the heater plate at step 32 or step 62. At step 63 or step 34 the controller determines the temperature response (i.e. the rate of change of temperature for cooling) of the chamber contents 8. Preferably at step 33 the controller measures the temperature at the end of the time period the power is switched off for (or varied). The controller determines one of two values, either the temperature change over a set time period (as per step 34), for example the controller may switch the power off to the heater plate and measure the drop of the temperature over a set time (as per steps 33 and 34). Alternatively the controller may measure the time taken for the temperature of the chamber contents 8 to drop to a certain specified temperature (as per step 63), for example the controller 11 may switch the heater plate off and measure the time it takes for the system to change in temperature by two degrees. Both of these determined values as per either method are indicative of rate of change of temperature for cooling. The amount of water remaining within the humidification chamber is determined by the controller (at step 35 or step 64) based on the rate of change of temperature change for cooling. Either method of determining rate of change of temperature can be used.

The level of water within the chamber during use is determined experimentally, meaning the relationship between the rate of change of temperature for cooling and the level of water is determined experimentally and stored within a further look up table. The look up table for water level during use is stored in the memory of the controller 11. The controller accesses the look up table to determine the level of water within the chamber. The controller varies the power and measures the change in temperature. The controller then determines the level of water within the chamber 5 by using the look up table to determine the value of water level based on the other variables identified earlier. Once the level of water is determined the power to the heater plate is restored to normal operating levels.

Figure 9:
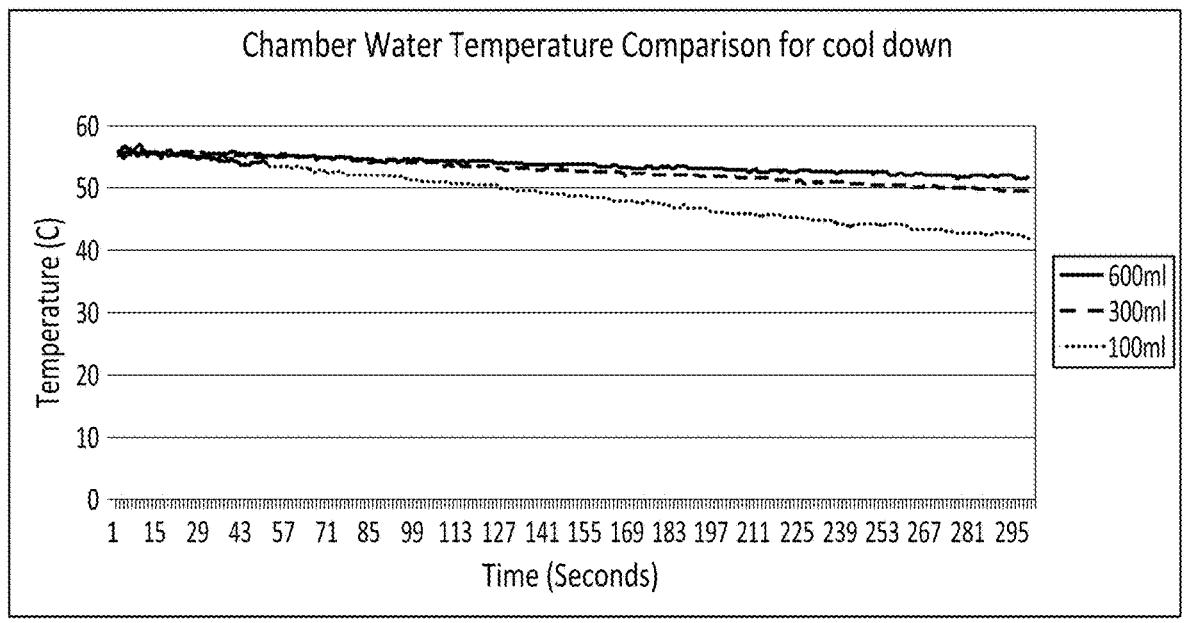
FIGS. 9 to 12 show experimental results of the temperature response when heater power is switched off, each of the figures showing temperature response for three volumes of water, where the temperature is measured at different positions in the system or humidifier.
Figure 10:
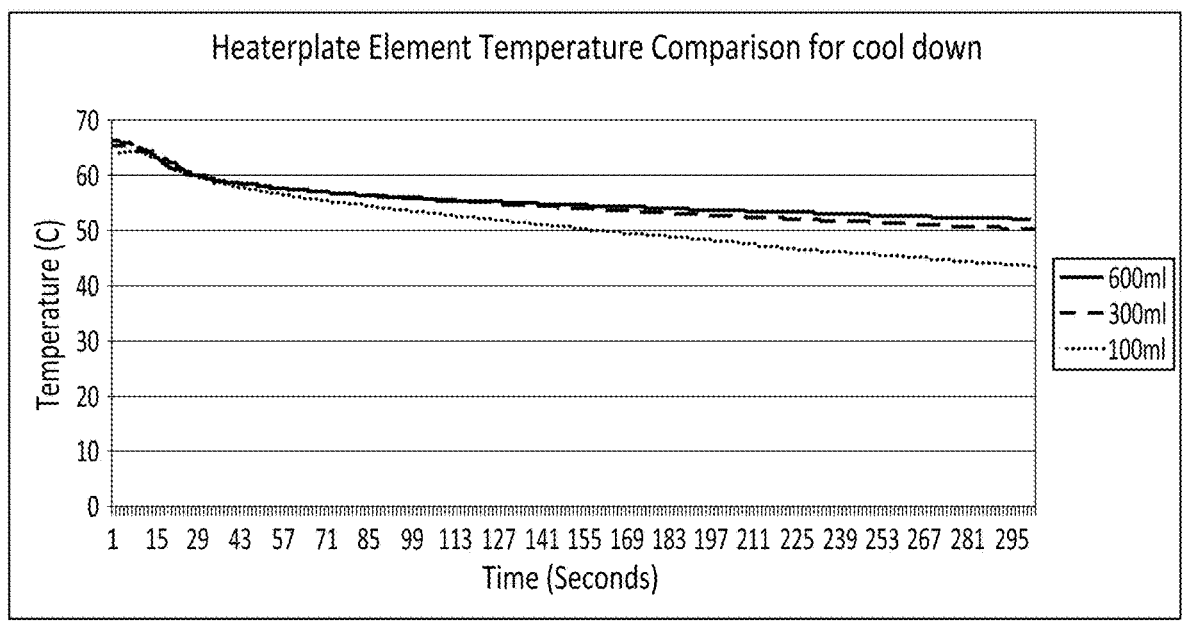
Figure 11:
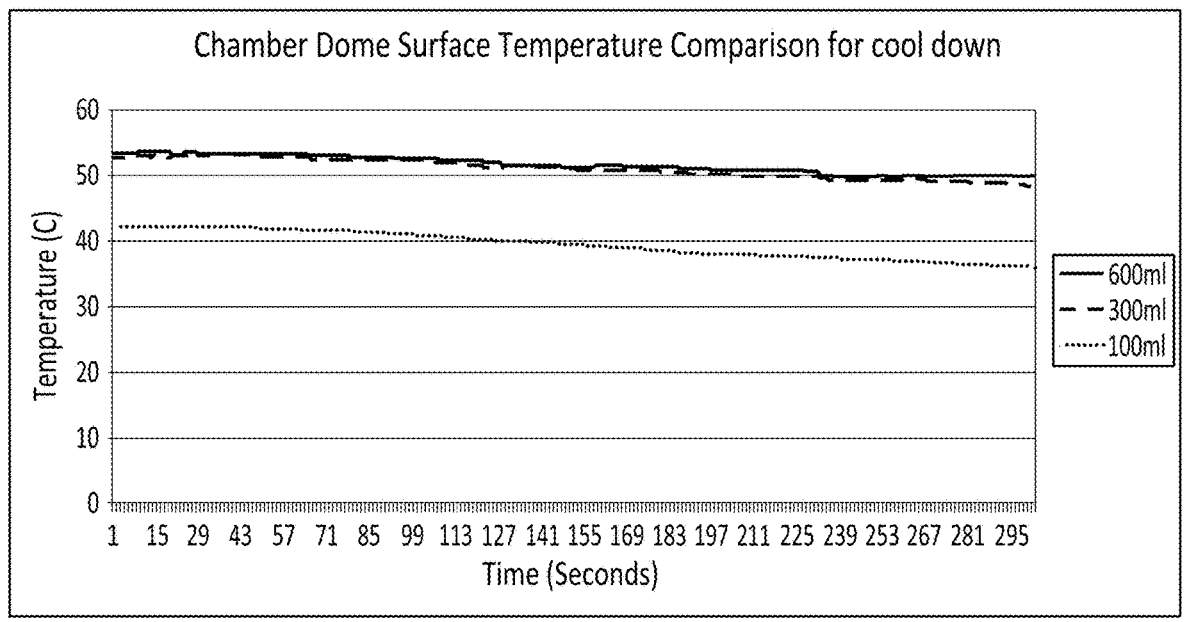
Figure 12:
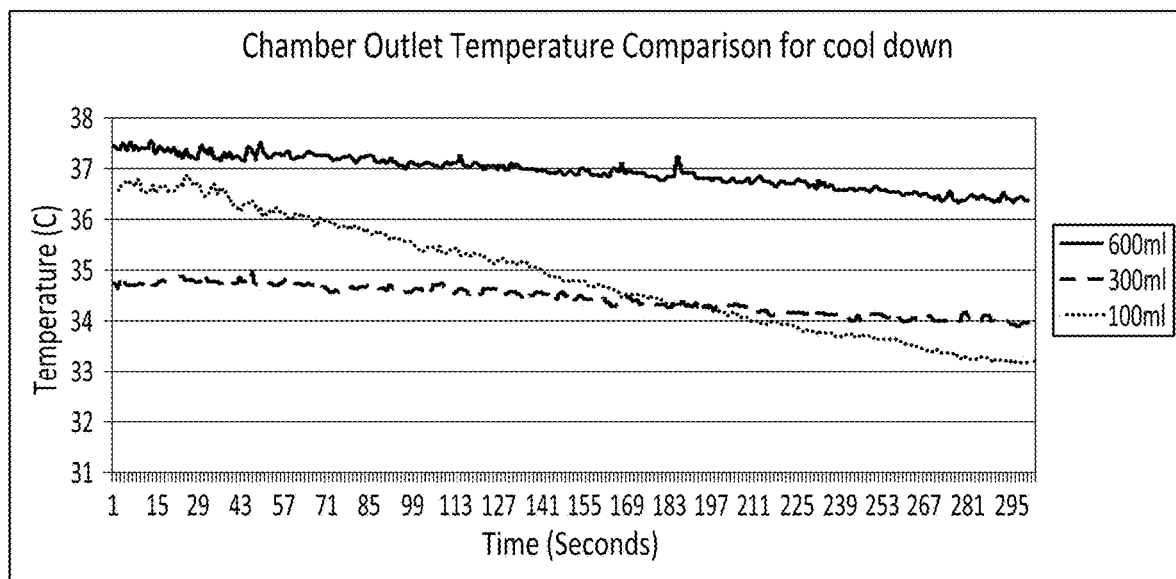

In the method of determining water level in use, the controller reduces the power to the heater plate or switches off the power to the heater plate and then measures the amount of temperature drop in a specified time interval. An alternative is the rate of change of temperature or to measure the time it takes for the temperature to drop a specified amount. The look up table preferably includes the relationship between water level and amount of temperature change for a specified time interval. The look up tables may be created based on experimental results of various rates of temperature change (i.e. cooling rates) for various volumes of water at various ambient conditions. Examples of experimental results used to create a lookup table are shown in FIGS. 9 to 12. The look up table relates the volume of water to the rate of change of temperature for cooling, as seen in FIGS. 9 to 12. The volume or level of water in the chamber can be measured or determined from the graph based on the cooling rate for that particular volume. Each volume of water in the chamber 5 has a different rate of cooling or a different temperature response for cooling, as seen from the three graphs that relate to the various volumes. The curves shown in FIGS. 9 to 12 are for 0 power delivered to the heater plate, i.e. the power is switched off. For clarity purposes only three volumes are shown in FIGS. 9 to 12. In the actual look up table the relationship between cooling rate and volume is determined for every operating volume of the chamber. Operational volumes or operational levels of water means the various water levels or volumes that are required during humidification. For example the minimum volume of chamber may be 10 ml and the maximum operational volume may be 800 ml. The temperature responses (i.e. cooling rates) are determined or resolved for every volume at 2 ml intervals from 10 ml to 800 ml. FIGS. 9-12 are one example showing three volumes 600 ml, 300 ml and 100 ml, but the temperature responses could be for any interval of volumes of water. Each volume of water has a unique cooling response (i.e. rate of change of temperature for cooling). The cooling rates are not dependent on the level of power if there is no power delivered to the heater. FIG. 9 shows the temperature response of the chamber water. FIG. 10 shows the temperature response of the heater plate temperature. FIG. 11 shows the temperature response of the chamber dome surface. FIG. 12 shows the temperature response at the chamber outlet. Any one or all of the temperature measurement locations may be used to measure temperature for any one of the methods described above. The figures confirm the relationship that the larger the volume of water the longer it takes to cool.

Alternatively the look up table may include an embedded formula that relates the rate of change of temperature, or the time taken for the temperature to reach a predetermined temperature and the level of water for various ambient conditions and flow rates. The controller runs the formula on sensor inputs of ambient conditions, temperature values or temperature rate of change, flow rates and time periods of heating and cooling. The embedded formula may be stored in the controller memory. The formula may be worked out and programmed into the controller.

The air flow rate can be determined using a flow sensor or pressure sensor placed near the inlet 4 of the chamber 5, where the chamber receives gases flow from a blower 2. In the most preferred form the flow sensor or pressure sensor is positioned right before the fan in the blower 2. Alternatively the sensor could be placed anywhere between the inlet 4 of the chamber 5 and the blower 2.

A further alternate method for calculating water level within the chamber during use will be described. The method involves energising the heater plate 9 to a specified level.

Water Evaporation Rate Calculation

Figure 8:
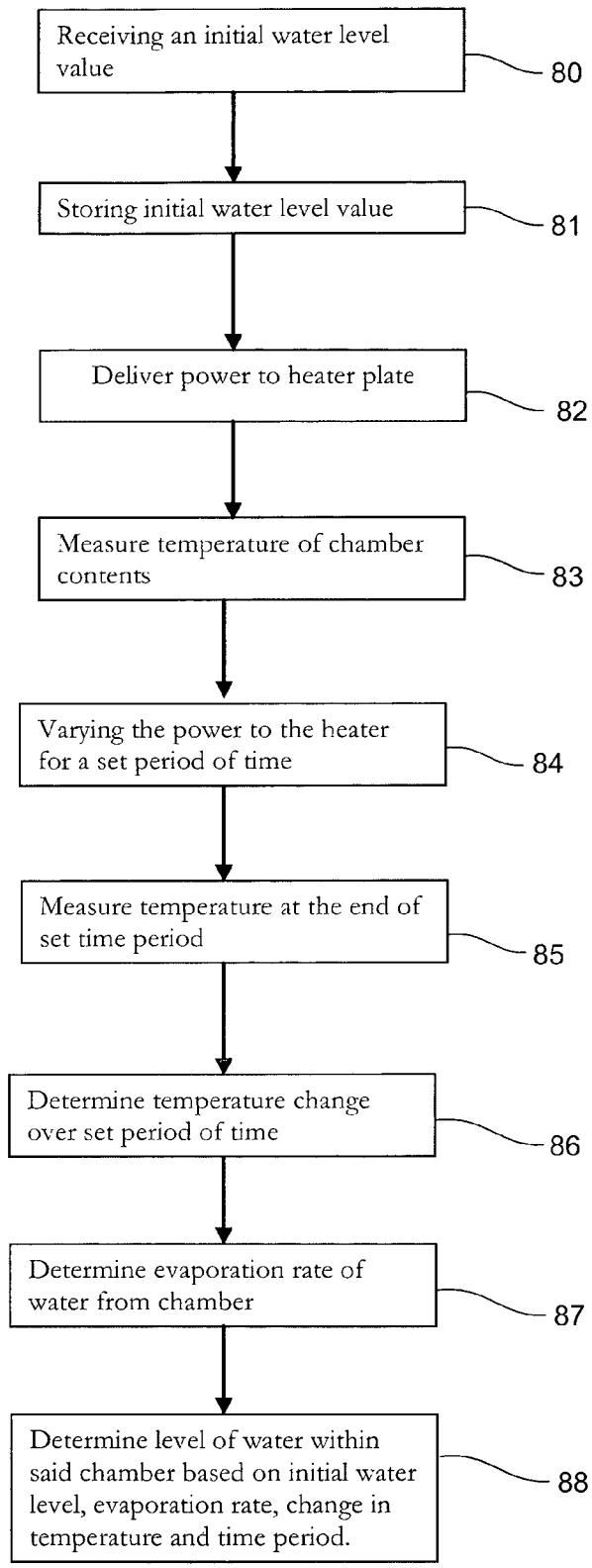
FIG. 8 shows a flow chart of a method for determining the level of water in a humidification chamber in use based on calculating evaporation rate and determining the level of water based on evaporation rate, initial water level and temperature change.

According to an alternate method for measuring water level during use the controller 11 calculates the amount of water consumption or evaporation rate in the humidifier chamber 5 and then calculates the level of water in the chamber using the amount of water consumed. FIG. 8 shows a flow chart of one method used to determine the level of water based on evaporation rate. The amount of water consumed is calculated as a rate of evaporation of water from the humidification chamber 5. The amount of water consumed or evaporation rate is based on ambient temperature, ambient humidity level, heater plate setting, air volume flow rate and wet surface area. The wet surface area may be the area of the reservoir in the chamber or the surface area of water within the chamber 5. Preferably the controller 11 directly measures ambient temperature, heater power and air flow rate. The controller 11 stores these values in memory and calls these values to determine the evaporation rate.

The evaporation rate can be calculated based on these inputs and the equation below:

$$M_B'' = \left(h_m \cdot \frac{M_b}{R_g}\right) \cdot A_{reservoir} \cdot (P_{Bi} - P_{Bo})$$

$M_B''$ = Evaporation Rate $M_B$ Molecular mass $R_g$ Universal gas constant $h_m$ Mass transfer coefficient $A_{reservoir}$ Wet surface area $P_{Bi}$ Vapour pressure for air stream $P_{Bo}$ Vapour pressure for wet surface The mass transfer coefficient $$\left(h_m \cdot \frac{M_b}{R_g}\right)$$

is calculated from the air volume flow rate and air flow pattern behaviour under different volume flow rate and water level. $A_{reservior}$ is a known input by knowing the chamber geometry. $P_{Bi}$ is the wet surface vapour pressure which would always be considered at saturated level. $P_{Bo}$ can be calculated by based on knowing the ambient humidity level. The ambient humidity level is preferably measured using a humidity sensor or any other suitable measuring device. This evaporation rate can be used to calculate the level of water within the chamber by subtracting the evaporation amount from the initial water level to result in the current water level value. This calculation can be performed as the system is operating. The controller preferably constantly runs this calculation of amount of water evaporated and maintains an estimate of the water level throughout the operating time of the humidification system. Most preferably the controller performs these calculations every few seconds for example every 30 seconds. Alternatively the controller could perform these calculations in minute intervals or any other suitable intervals. The initial level of water within the chamber can be determined using any one of the methods for determining water level upon start up as described earlier. Alternatively the user may input the initial level of water in the chamber through the user interface 22. The initial level of water in the chamber is stored in memory and called by the controller to determine level of water in the chamber using the evaporation rate.

The evaporation rate method can be used in a CPAP system or humidification system to determine the water level in the chamber 5 and provide a more accurate level of water within the chamber 5. The evaporation rate can be used with any one of the methods for determining the level of water in the chamber in use to provide a more accurate value of water level in the chamber 5. The water level in the chamber during use or at start up is calculated and stored based on of the method described earlier. At steps 80 and 81 the controller receives an initial water level and stores the initial water level. At step 82 the controller delivers power to the heater. At step 83 the controller determines the chamber contents temperature. At step 84 the controller varies the power delivered to the heater. At step 85 the controller measures the temperature at the end of the period of varied power. At step 86 the rate of change of temperature or temperature change or temperature response is determined. The evaporation rate is calculated at step 87, using the method for calculating evaporation rate based on the formula identified above. The actual level of water is calculated at step 88 based on the evaporation rate, initial water level, change in temperature and time period. Preferably the evaporation rate is used to calculate an actual evaporation amount that can be used to determine water level by subtracting evaporation amount from the level of water calculated by the method for determining level of water in use. The evaporation amount is determined based on the evaporation rate and a set time period, i.e. the evaporation amount is equal to the evaporation rate multiplied by the time period. Alternatively the controller may determine the level of water from a look up table that relates the calculated water level, initial water level, temperature change and the evaporation rate. The look up table gives the "true water" level value in the chamber. The true water level value is the water level once the evaporation rate of water has been accounted or compensated for. The look up table includes the relationship between calculated water level and the evaporation rate. The look up table determining the true water level may also be stored in the memory associated with the controller.

Advantages

Determining the water level in the humidification chamber 5 is useful because it allows the a CPAP machine or the gases delivery system to include a water level indicator that prompts a user or hospital worker to refill the chamber when the water level is too low. This is advantageous because the water level measurement method described can be implemented on machines where the humidification chamber is not visible and a user cannot tell the level of water in the chamber 5 by looking at the chamber. The controller can alert the user to fill the chamber 5 prior to use. Alternatively the controller can alert the user to a low water level during use of the humidification chamber. The controller can serve as a low water level alarm. For example the controller may activate a buzzer or siren to warn a user of low water level. This is particularly useful at start up of the device since the controller can warn a user not to start the device if the water level is too low. The methods identified above are also advantageous because it allows control of the water consumption within the humidification chamber. The controller can vary the heat of the heater plate and the flow rate of gases to ensure the water lasts longer based on the amount of humidity required and the duration of humidification. The controller may be capable of learning the therapy regime of a particular patient based on the water consumption and water level calculations through the therapy. Alternatively the controller may be pre-programmed with a patient's therapy regime for a night for example the flow rates and the humidity levels. The controller can monitor the water level and control the water level to ensure the patient receives some humidification throughout the therapy.

In the preferred form the controller maintains a record of the nominal treatment time for a patient. Preferably the nominal treatment time for a patient is based on a historical record of patient treatment time. The controller may monitor patient treatment times and store patient treatment times in memory. The treatment times may be stored in a lookup table or any other suitable form. The nominal patient treatment time is calculated based on the stored historical values by any appropriate method.

Alternatively the treatment time for the patient may be pre-programmed into the controller 11 and stored in memory. Alternatively the patient or a health worker or any other user may manually input a patient's treatment time into the controller through the user interface 22. In a further alternative form the humidification device 10 may include a USB port and a patient's treatment information may be programmed into the controller with a USB. In a further alternative form the humidifier or humidification device 10 or controller 11 may include a wireless communication apparatus like a modem. The wireless communication apparatus may allow the controller to communicate with a server that is offsite. The controller may receive a patient's treatment time and details from the server by wireless communication using any appropriate wireless communication protocol.

The controller can monitor the level of water in the chamber using one of the methods described earlier. The controller 11 can control the heating of the heater plate such that the volume of water within the chamber 5 lasts the entire time of the treatment or at least a substantial time of the treatment, while also providing a minimum amount of humidification to the patient. The minimum amount of humidification to a patient is any humidity level above ambient humidity. This is advantageous because it stops drying of the patient's airways. In an alternative form the amount of humidity to be delivered to a patient may be received by the controller 11 and stored in the controller 11. The amount of humidity to be delivered to a patient may be part of the patient's treatment data that is received and stored by the controller 11. The controller 11 also monitors the water level in the chamber during the treatment. If the water level in the chamber 5 drops below a minimum water level the controller can alert the user or switch off the power to the heater plate. In another form the controller 11 may measure the level of water in the chamber 5 prior to beginning the treatment. The controller 11 may determine if the amount of water is enough to last the entire treatment. If there is enough water in the chamber 5 the controller will begin the treatment. If the controller determines the water level is too low or below a minimum water level the controller can alert the user via an alarm or a message on the screen. The controller only alerts the user of low water level at the start of the treatment or in the early stages of treatment. The early stages of treatment are considered up to the first ten minutes of treatment. If the controller detects low water level during treatment after the first ten minutes the controller reduces the power to the heater in an attempt to maintain a minimum humidity level while making the water in the chamber 5 last. If however the controller 11 detects the water level is too low during treatment the controller 11 may switch off the power to the heater.

CPAP treatment is preferably delivered to a patient while the patient is asleep. It is therefore advantageous to automatically measure or calculate the level of water in the humidification chamber 5, because the patient does not need to constantly wake up and measure the volume of water left in the chamber. The methods described earlier are also advantageous because the controller 11 regulates power to the heater plate such that the water in the chamber 5 lasts for at least the nominal treatment time while providing the patient with a minimum level of humidification. This is advantageous because the patient is provided with humidification while the patient is asleep which means the patient's airways are not dried and patient is not woken from sleep. The controller alarms or alerts the user of a low water level before treatment or in the early stages of treatment. This is advantageous because the controller alerts the user of a low water level before the user is sleeping and hence allows the user the chance to refill the chamber 5. During treatment if a low water level is detected the controller 11 simply switches off power to the heater or reduces power to the heater in order to conserve the water in the chamber. This advantageous because the patient is not woken by an alarm and the reduced power may still allow the controller 11 to deliver a minimum level of humidification thus reducing the drying of the patient's airways.

Using the evaporation rate along with one of the methods to determine the level of water in the chamber provides a more accurate value of water in the chamber. The true water level that can be determined using the evaporation rate along with one of the methods for determining water level provides for a more accurate value of water level in the chamber 5. This is advantageous because it allows for finer control and allows for more accurate monitoring of the water level in the chamber. The more accurate values also prevent false alarms of low water level. This means the user is alerted when the water level is low and the user does not need to constantly monitor the water level in the chamber 5.

In the preferred form the humidifier or system includes a humidity sensor (not shown) located in the ambient gases, for example the gases flow prior to the chamber entrance. This is to improve the accuracy of the method of water level determination implemented by the controller 11. In a controller 11 for use with a ventilator the controller 11 may be programmed to assume that the initial humidity of the gases is zero.

The method of determining water level is accurate for high chamber water levels, meaning when the chamber is full or close to full. The applicant has found through testing the accuracy of the water level determination method decreases as the water level within the chamber 5 drops. The method is more inaccurate at low levels of water within the chamber than at high levels of water within the chamber. Adding a humidity sensor allows the controller to measure the humidity at the inlet of the chamber and measure the humidity of the inlet gases. This allows the controller 11 to calibrate itself and therefore results in more accurate results at lower water levels within the chamber.

Chamber Refill Verification

In a further aspect a humidity sensor 21 could be used downstream of the chamber. The CPAP device may also include a user interface 22 that allows the user to enter information. The controller receives user inputs through the user interface. The controller runs a method to check whether the humidification chamber 5 has been filled by the user. The method involves using the information from the downstream humidity sensor in combination with a user input.

The controller asks the user if the "chamber has been filled?" The messages to the user may be displayed on a display 23 like an LCD screen or any other appropriate screen. Preferably the user interface has at least a YES and NO button to allow the user to respond to the question of whether the chamber has been refilled. The user either pushes the YES or NO button to indicate either the chamber has been filled or not.

The controller continuously monitors the value of the humidity sensor placed downstream of the chamber 5. The humidity sensor 21 measures the value of humidity in the gases exiting the chamber because it is placed downstream of the chamber 5 and preferably in the flow path of the gases exiting the chamber 5. The controller maintains an estimate of the water level in the chamber based on the humidity value minus the humidity of gases entering the chamber. The controller can verify if the chamber has been filled or not and hence can activate a warning to the user if the chamber has not been filled enough. The controller will be pre-programmed with a minimum threshold humidity value that relates to the minimum water level within the chamber 5. The controller may include a look up table relating the downstream humidity sensor 21 values and water level within the chamber. The look table allows the controller to determine a water level estimate based on the humidity value and vice versa. This look up table can be created and programmed into the controller memory based on experimental data. The look up table also allows the controller to check that the downstream humidity sensor 21 is operating correctly and not giving false readings. If false readings are determined by the controller the controller can alert the user that the downstream humidity sensor is faulty.

Relative Humidity Calculation

The controller 11 has a variety of functions besides the water level measurement methods described above. The controller 11 is also configured to calculate the relative humidity of a room. The controller 11 calculates this relative room humidity or ambient humidity based on the water consumption in the humidification chamber. The relative humidity of a room is calculated by calculating the mass transfer into the air stream. The mass transfer into the airstream is related to the ambient humidity, flow rate of gases, temperature, and the heater plate settings, like the amount of heat energy. This relationship is preferably determined experimentally and stored in a look up table and stored within the controller's memory.

The controller 11 refers to the look table and determines an estimate of the ambient humidity for a given water consumption value at a given flow rate, temperature and heating value. Alternatively the relative humidity can be calculated by reversing the equation for water consumption and calculating the relative humidity or ambient humidity based on the value of water consumption.

In a further alternative the value of water consumption can be resolved from the evaporation rate calculation as described earlier. The evaporation rate is directly proportional to the water consumption rate from the humidification chamber 5. The water consumption rate may also be calculated using any one of the methods for determining water level within the humidification chamber. Preferably the value of water consumption is determined by calculating the difference between successive water level values. The method for determining water level within a humidification chamber 5 is preferably repeatedly run to continuously monitor the amount of water in the chamber 5. The controller stores consecutive values of water level within the chamber and calculated water consumption based on the consecutive values of water level in the chamber. As another alternative method the value of water consumption can be calculated using a combination of one of the methods for determining water level and the method for calculating evaporation rate. The water level in the chamber can be calculated and stored repeatedly using one of the methods described earlier. The evaporation rate of water can be calculated and subtracted from a previous or initial water level to give a true water level value. The water consumption can be calculated as a difference between two consecutive calculated water level values. In a further alternative the water level may be measured by a level sensor or any other appropriate sensor. The sensor preferably measures the water level at specified time intervals and stores water level values in memory. The water consumption value can be calculated as a difference between two consecutive measured water level values. The controller 11 preferably calculates water consumption value.

The controller being able to calculate the ambient humidity or relative humidity allows the use of climate settings in a CPAP control algorithm. This allows the controller to adjust the other parameters of the CPAP device based on the climate settings and relative humidity of the room. Knowing the ambient humidity allows for more accurate control of the CPAP device. This method of determining the relative humidity also allows the controller to optimise the heater plate temperature based on the relative humidity value and hence allows better control of the humidity level in the gases delivered to the patient.

The controller may include several look up tables. The controller selects and uses the correct look up table based on the mode of operation of the system. The basic modes of operation are "start up", "in use" and "relative humidity recognition". The user may manually select the operation mode of the system or the controller may operate and select the appropriate mode automatically.

For any description in this specification of using a look up table for determining water level in the chamber based on temperature change of the water, the controller may store multiple look up tables for various ambient temperature and ambient air flow. The controller may also store multiple look up tables for various ambient humidity values. The controller can select the appropriate look up table based on the air flow or ambient temperature measurement. The ambient temperature and air flow can be measured by an appropriate sensor. The controller selects the look up table based on either ambient temperature, air flow, ambient humidity or a combination of these. The look up tables are preferably built based on experimental results.

The steps of the methods described above are preferably executed in a sequential manner. The steps are preferably performed independent of each other. Alternatively in some embodiments some of the method steps may be performed simultaneously by the controller 11, while still achieving the desired result. In a further alternative some of the steps may be performed out of the order described but still achieve the same result and remain within the scope of the invention.

While the invention is susceptible to embodiment in different forms, specific embodiments are shown in the drawings, and described in detail above. The present disclosure is to be considered an exemplification of the principles of the invention, and is not intended to limit the invention to that as illustrated and described herein.

What is claimed is:

1. A method of electronically determining a water level in a chamber within a humidified gases delivery system configured to provide humidified respiratory gases to a user in a respiratory treatment, wherein water in the chamber is configured to humidify the respiratory gases, the method comprising:
    using an electronic controller of the system:
        determining an evaporation rate of the water in the chamber during the respiratory treatment;
        determining a current water level based at least in part on the evaporation rate;
        determining a remaining treatment time of the respiratory treatment; and
        based at least in part on the evaporation rate, the current water level, and the remaining treatment time:
            calculating a remaining time that humidity can be provided to the respiratory gases by the water in the chamber so as to determine whether the current water level can last the remaining treatment time, and
            upon determining that the current water level cannot last the remaining treatment time, adjusting control of power supplied to a heater plate of the system so as to prolong a time period when the respiratory gases are humidified by the current water level while providing at least a minimum amount of humidification to the respiratory gases, wherein the heater plate is powered to heat up the water in the chamber to create water vapor.

2. The method of claim 1, further comprising outputting a low water level alert in response to determining that the current water level is insufficient to last the remaining treatment time.

3. The method of claim 1, wherein calculating the remaining time is performed at a start of the respiratory treatment.

4. The method of claim 1, wherein the determination of the evaporation rate is based at least in part on one or more of an ambient temperature, the power supplied to the heater plate, or an air flow rate.

5. The method of claim 1, further comprising determining an evaporation amount based on the evaporation rate in a set time period.

6. The method of claim 5, wherein the current water level is determined by subtracting the evaporation amount from an initial water level value.

7. The method of claim 6, further comprising receiving the initial water level value via a user input or a sensor.

8. The method of claim 1, wherein the current water level is determined by using a look up table that stores a plurality of values corresponding to a relationship between the evaporation rate and known water levels in the chamber.

9. The method of claim 8, wherein the look up table is stored in a memory of the electronic controller.

10. The method of claim 1, wherein the minimum amount of humidification is a humidity level above ambient humidity.

11. A humidified gases delivery system configured to provide humidified respiratory gases to a user in a respiratory treatment, the system comprising:
    a chamber configured to hold a volume of water, wherein the water is configured to humidify the respiratory gases;
    a heater plate configured to be powered to heat up the water in the chamber to create water vapor;

an electronic controller configured to control the power supplied to the heater plate, wherein the electronic controller is further configured to:
  determine an evaporation rate of the water in the chamber during the respiratory treatment;
  determine a current water level based at least in part on the evaporation rate;
  determine a remaining treatment time of the respiratory treatment; and
  based at least in part on the evaporation rate, the current water level, and the remaining treatment time:
    calculate a remaining time that humidity can be provided to the respiratory gases by the current water level so as to determine whether the current water level can last the remaining treatment time, and/or
    upon determining that the current water level cannot last the remaining treatment time, adjust control of the power supplied to the heater plate so as to prolong a time period when the respiratory gases are humidified by the current water level while providing at least a minimum amount of humidification.

12. The system of claim 11, wherein the electronic controller is further configured to output a low water level alert in response to determining that the current water level is insufficient to last the remaining treatment time.

13. The system of claim 11, wherein the electronic controller is configured to calculate the remaining time at a start of the respiratory treatment.

14. The system of claim 11, wherein the electronic controller is configured to determine the evaporation rate based at least in part on one or more of an ambient temperature, the power supplied to the heater plate, or an air flow rate.

15. The system of claim 11, wherein the electronic controller is further configured to determine an evaporation amount based on the evaporation rate in a set time period.

16. The system of claim 15, wherein the current water level is determined by subtracting the evaporation amount from an initial water level value.

17. The system of claim 16, wherein the electronic controller is further configured to receive the initial water level value via a user input or a sensor.

18. The system of claim 11, wherein the current water level is determined by using a look up table that stores a plurality of values corresponding to a relationship between the evaporation rate and known water levels in the chamber.

19. The system of claim 18, wherein the look up table is stored in a memory of the electronic controller.

20. The system of claim 11, wherein the minimum amount of humidification is a humidity level above ambient humidity.

* * * * *

UNITED STATES PATENT AND TRADEMARK OFFICE
CERTIFICATE OF CORRECTION

| | | |
|---|---|---|
| PATENT NO. | : 11,980,719 B2 | Page 1 of 1 |
| APPLICATION NO. | : 17/445808 | |
| DATED | : May 14, 2024 | |
| INVENTOR(S) | : Alastair Edwin McAuley et al. | |

It is certified that error appears in the above-identified patent and that said Letters Patent is hereby corrected as shown below:

In the Claims

In Column 23 at Line 16, in Claim 11, delete "and/or" and insert -- and --.

Signed and Sealed this
Tenth Day of September, 2024

Katherine Kelly Vidal
*Director of the United States Patent and Trademark Office*